United States Patent
Gambale et al.

(10) Patent No.: US 6,517,527 B2
(45) Date of Patent: Feb. 11, 2003

(54) TRANSTHORACIC DRUG DELIVERY DEVICE

(75) Inventors: Richard A. Gambale, Tyngsboro, MA (US); Stephen J. Forcucci, Arlington, MA (US); Richard T. Choh, Lowell, MA (US); Robert Cafferata, Belmont, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/888,750

(22) Filed: Jun. 25, 2001

(65) Prior Publication Data

US 2001/0037086 A1 Nov. 1, 2001

Related U.S. Application Data

(62) Division of application No. 09/164,164, filed on Sep. 30, 1998, now Pat. No. 6,251,079.

(51) Int. Cl.[7] .............................................. A61M 31/00
(52) U.S. Cl. ...................................................... 604/508
(58) Field of Search ................................ 600/468, 486, 600/487, 508; 607/120; 604/264, 181, 187, 523, 528

(56) References Cited

U.S. PATENT DOCUMENTS

| | | | |
|---|---|---|---|
| 3,680,544 A | | 8/1972 | Shinnick et al. |
| 3,773,034 A | * | 11/1973 | Burns et al. ............... 128/4 |
| 3,991,750 A | | 11/1976 | Vickery |
| 4,217,911 A | | 8/1980 | Layton |

(List continued on next page.)

FOREIGN PATENT DOCUMENTS

| | | |
|---|---|---|
| DE | 296 19 029 U1 | 4/1997 |
| EP | 0 132 387 | 1/1985 |
| EP | 0 363 661 | 1/1985 |

(List continued on next page.)

OTHER PUBLICATIONS

Joachim Burhenne, "Less Invasive Medicine: Historical Perspectives", *Boston Scientific Online*, www.bsci.com/corproate/special report1.html: May 20, 1999, pp. 1–8.

(List continued on next page.)

*Primary Examiner*—Sharon Kennedy
(74) *Attorney, Agent, or Firm*—Kirkpatrick & Lockhart LLP

(57) ABSTRACT

The present invention provides a transthoracic drug delivery device that utilizes pressure to determine the precise location of the distal tip of the delivery tube of the device to insure that therapeutic substances are ejected into the myocardium and not dissipated in unintended tissue locations. In one embodiment the drug delivery device comprises a pressure sensing tube mounted in parallel to a drug delivery tube wherein the tubes are staggered so that the pressure tube extends beyond the delivery tube. When the myocardium is penetrated by the tubes, advancement into the heart and penetration into the left ventricle by the pressures sensing tube results in a pressure increase that indicates to the physician that the drug delivery tube, by its placement relative to the pressure sensing tube is still in the myocardium and, thus, prepared to deliver the drug. In another embodiment, a steerable syringe is provided so that multiple sites in the myocardium can be treated with a therapeutic substance with only one penetration into the heart. Once the delivery tube of the syringe penetrates the left ventricle, its distal tip can be deflected back toward the endocardial surface and the tube withdrawn proximally to cause penetration of the tip into the myocardium. A pressure sensor mounted to the tube indicates, by a measured drop in pressure that the myocardium has been penetrated. The therapeutic substance is ejected into the myocardium and the device is then backed out of the tissue by advancing the syringe in a distal direction. The deflectable tip can be adjusted to a different deflection angle and the delivery tube rotated to make available a circular array of points that may be accessed by the syringe.

4 Claims, 5 Drawing Sheets

U.S. PATENT DOCUMENTS

| | | | |
|---|---|---|---|
| 4,451,253 A | 5/1984 | Harman | |
| 4,461,280 A | 7/1984 | Baumgartner | |
| RE31,873 E | 4/1985 | Howes | |
| 4,551,129 A | 11/1985 | Coleman et al. | |
| 4,586,923 A * | 5/1986 | Gould et al. | 604/95 |
| 4,700,692 A | 10/1987 | Baumgartner | |
| 4,718,425 A | 1/1988 | Tamaka et al. | |
| 4,774,949 A | 10/1988 | Fogarty | |
| 4,808,164 A | 2/1989 | Hess | |
| 4,894,057 A | 1/1990 | Howes | |
| 4,901,931 A | 2/1990 | Millar | |
| 4,917,666 A | 4/1990 | Solar et al. | |
| 4,920,980 A | 5/1990 | Jackowski | |
| 5,269,326 A | 12/1993 | Verrier | |
| 5,284,138 A | 2/1994 | Kujawski | |
| 5,287,861 A | 2/1994 | Wilk | |
| 5,328,470 A | 7/1994 | Nabel et al. | |
| 5,380,316 A | 1/1995 | Alta et al. | |
| 5,389,096 A | 2/1995 | Alta et al. | |
| 5,405,376 A | 4/1995 | Mulier et al. | |
| 5,409,019 A | 4/1995 | Wilk | |
| 5,429,144 A | 7/1995 | Wilk | |
| 5,452,733 A | 9/1995 | Sterman et al. | |
| 5,454,374 A | 10/1995 | Omachi | |
| 5,487,739 A | 1/1996 | Aebischer et al. | |
| 5,501,664 A | 3/1996 | Kaldany | |
| 5,514,130 A | 5/1996 | Baker | |
| 5,562,613 A | 10/1996 | Kaldany | |
| 5,562,922 A | 10/1996 | Lambert | |
| 5,614,206 A | 3/1997 | Randolph et al. | |
| 5,629,008 A | 5/1997 | Lee | |
| 5,655,548 A | 8/1997 | Nelson | |
| 5,656,029 A | 8/1997 | Imran et al. | |
| 5,662,124 A | 9/1997 | Wilk | |
| 5,666,970 A | 9/1997 | Smith | |
| 5,682,906 A | 11/1997 | Sterman et al. | |
| 5,701,905 A | 12/1997 | Esch | |
| 5,744,515 A | 4/1998 | Clapper | |
| 5,755,682 A | 5/1998 | Knudson et al. | |
| 5,756,127 A | 5/1998 | Grisoni et al. | |
| 5,769,843 A | 6/1998 | Abela et al. | |
| 5,810,836 A | 9/1998 | Hussein et al. | |
| 5,830,502 A | 11/1998 | Dong et al. | |
| 5,833,645 A | 11/1998 | Lieber et al. | |
| 5,840,059 A | 11/1998 | March et al. | |
| 5,971,993 A | 10/1999 | Hussein et al. | |
| 5,972,013 A | 10/1999 | Schmidt | |
| 5,980,548 A | 11/1999 | Evans | |
| 6,004,269 A * | 12/1999 | Crowley et al. | 600/439 |
| 6,030,360 A * | 2/2000 | Biggs | 604/95 |
| 6,045,565 A | 4/2000 | Ellis et al. | |
| 6,126,633 A * | 10/2000 | Kaji et al. | 604/95.04 |

FOREIGN PATENT DOCUMENTS

| | | |
|---|---|---|
| EP | 0 490 459 A1 | 6/1992 |
| EP | 0 717 969 A2 | 6/1996 |
| EP | 0 830 873 A2 | 3/1998 |
| EP | 0 853 921 A2 | 11/1999 |
| EP | 0 953 320 A2 | 11/1999 |
| WO | WO 90/06723 | 6/1990 |
| WO | WO 94/05265 | 3/1994 |
| WO | WO 94/27612 | 12/1994 |
| WO | WO 95/33511 | 12/1995 |
| WO | WO 96/20698 | 7/1996 |
| WO | WO 97/16169 | 10/1996 |
| WO | WO 96/39830 | 12/1996 |
| WO | WO 96/40368 | 12/1996 |
| WO | WO 97/42910 | 7/1997 |
| WO | WO 97/38730 | 10/1997 |
| WO | WO 97/45105 | 12/1997 |
| WO | WO 97/47253 | 12/1997 |
| WO | WO 98/05307 | 2/1998 |
| WO | WO 98/16644 | 4/1998 |
| WO | WO 89/23228 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |

OTHER PUBLICATIONS

Charles T. Dotter, "Transluminally–Placed Coilspring Endarterial Tube Grafts, Long–Term Patency in Canine Popliteal Artery", *Investigative Radiology*, Sep.–Oct. 1969, vol. 4, pp. 329–332.

Raymond G. McKay, "Catheter–Based Techniques of Local Drug Delivery", *The New Manual of Interventional Cardiology*, 1966, pp. 645–660.

Alfred Goldman, "Experimental Methods for Producing a Collateral Circulation to the Heart Directly From the Left Ventricle", *J. Thoracic Surg.*; Mar. 1956; vol. 31, No. 3, pp. 364–374.

Vallavan Jeevanandam, "Myocardial Revascularization by Laser–Induced Channels", *Surgical Forum*, American College of Surgeons 76$^{th}$ Clinical Congress, pp. 225–227.

A. Hassan Khazei et al., "Myocardial Canalization, A New Method of Myocardial Revascularization", *The Annals of Thoracic Surgery*, vol. 6, No. 2, Aug. 1968; pp. 163–171.

Ladislav Kuzela et al., "Experimental Evaluation of Direct Transventricular Revascularization", *Journal of Thoracic and Cardiovascular Surgery*, vol. 57, No. 6, Jun. 1969.

C. Massimo et al., "Myocardial Revascularization by a New Method of Carrying Blood Directly From the Left Ventricular Cavity Into the Coronary Circulation", *Journal Thoracic Surgery*, Aug. 1957, pp. 257–264.

A. Michael Lincoff et al., "Local Drug Delivery for the Prevention of Restenosis: Fact, Fancy and Future", *Circulation*, vol. 90, No. 4, Oct. 1994.

M. Mirhoseini et al., "Revascularization of the Heart by Laser", *Journal of Microsurgery* (1981) 2:253–260.

M. Mirhoseini, "Myocardial Revascularization by Laser: A Clinical Report", *Lasers in Surgery and Medicine* (1983) 3:241–245.

Reimer Riessen et al., "Prospects for Site–Specific Delivery of Pharmacologic and Molecular Therapies", *JACC*, vol. 23, No. 5, Apr. 1994:1234–44.

P.K. Sen et al., "Transmyocardial Acupuncture a New Approach to Myocardial Revascularization", *Journal of Thoracic and Cardiovascular Surgery*, vol. 50, No. 2, Aug. 1965.

Bruce F. Waller, "Anatomy, Histology, and Pathology of the Major Epicardial Coronary Arteries Relevant to Echocardiographic Imaging Techniques", vol. 2, No. 4, Jul.–Aug. 1989, pp. 232–252.

P. Walter et al., "Treatment of Acute Myocardial Infarction by Transmural Blood Supply From the Ventricular Cavity", *Europ. Surg. Res.* 3:130–138 (1971).

Robert L. Wilensky et al., "Methods and Devices for Local Delivery in Coronary and Peripheral Arteries", *TCM*, vol. 3, No. 5 (1993), pp. 163–170.

R–K Li et al., "Cell Therapy to Repair Broken Hearts", *Can J. Cardiology* 1998: 14(5):735–744.

Zhai, Y. et al., "Inhibition of Angiogenesis and breast Cancer Xenograft Tumor Growth by Vegi, A Novel Cytokine of the TNK Superfamily", *Int. J. Cancer* 1999, Jul. 2;82(1):131–6.

Warejcka, DJ et al., "A Population of Cells Isolated From Rat Heart Capable of Differentiating Into Several Mesodermal Phenotypes", *J. Surg. Res.*, May 1996;62(2):233–242.

Braun T, Arnold, "MYF–5 and MYOD Genes are Activated in Distinct Mesenchymal Stem Cells and Determine Different Skeletal Muscle Cell Lineages", *Emo J* 1966 Jan. 15;15(2):310–318.

Wakitani, S. et al., "Myogenic Cells Derived from Rat Bone Marrow Mesenchymal Stem Cells Exposed to 5–Azacytidine", *Muscle Nerve*, Dec. 1995; 18(12):1417–1426.

Yamaguchi, A., "regulation of Differentiation Pathway of Skeletal Mesenchymal Cells in Cell Lines by Transforming Growth Factor–Beta Superfamily", *Semin Cell Biol.*, Jun. 1995:6(3):165–173.

Chiu, R.C., et al., "Cellular Cardiomyoplasty: Myocardial Regeneration with Satellite Cell Implantation", *Ann Thorac Surg*, Jul. 1995:60(1):12–18.

Gulati, A.K., "Regeneration Pattern of Cardiac and Skeletal Muscle After Transplantation Into a Skeletal Muscle Bed in Rats", *Anat. Rec.*, Jun. 1995:242(2):188–194.

Tam, S.K., et al., "Cardiac Myocyte Terminal Differentiation, Potential for Cardiac Regeneration", *Ann NY Acad. Sci*, Mar. 27, 1995; 752:72–79.

Mima, T. et al., "Fibroblast Growth Factor Receptor is Required for In Vivo Cardiac Myocyte Proliferation at Early Embryonic States of Hear Development", *Proc. Natl. Acad. Sci. USA*, Jan. 17, 1995; 92(2):467–471.

Butler, R., Evidence for a Regenerative Capacity in Adult Mammalian Cardiac Myocytes, *Am. J. Physiol.*, Mar. 1989;256(3 Pt. 2):R797–R800.

B. Schumacher, "Induction of Neoangiogenesis in Ischemic Myocardium by Human Growth Factors, First Clinical Results of a New Treatment of Coronary Heart Disease", *Clinical Investigation and Reports*, pp. 645–650, Dec. 1997.

Ladislav Juzela et al., experimental Evaluation of Direct Transventricular Revascularization, *Journal of Thoracic Cardiovascular Surgery*, vol. 57, No. 6, pp. 770–773, Jun. 1969.

Mahmood Mirhoseini et al., Revascularization of the Heart by Laser, *Journal of Microsurgery*, pp. 253–260, Jun. 1981.

Michael P. Macris et al., "Minimally Invasive Access of the Normal Pericardium: Initial Clinical Experience with a Novel Device", *Clin. Cardiol.*, vol. 22, (Supp I), pp. I–36–I–39 (1999).

P.K. Send et al., "Transmyocardial Acupuncture: A New Approach to Myocardial Revascularization", *Journal of Cardiovascular Surgery*, pp. 181–189, Aug. 1965.

Peter Whittaker et al., "Transmural Channels Can protect Ischemic Tissue, Assessment of Long–Term Myocardial Response to Laser and Needle–Made Channels", *Circulation*, vol. 93, No. 1, pp. 143–152, Jan. 1996.

Roque Pifarre et al., "Myocardial Revascularization by Transmyocardial Acupuncture: A physiologic Impossibility", *Journal of Thoracic and Cardiovascular Surgery*, vol. 58, No. 3, pp. 424–429, Sep. 1969.

Neil B. Ingels, et al., "Measurement of Midwall Myocardial Dynamics in Intact Man by Radiography of Surgically Implanted Markers", *Circulation*, vol. 52, pp. 859–867 (Nov. 1975).

* cited by examiner

TRANSTHORACIC DRUG DELIVERY DEVICE

RELATED APPLICATION

This application is a divisional of application Ser. No. 09/164,164 filed Sep. 30, 1998, now U.S. Pat. No. 6,251,079, issued Jun. 26, 2001.

FIELD OF THE INVENTION

The present invention relates to a device and method for delivering a therapeutic substance to the myocardium of a human heart.

BACKGROUND OF THE INVENTION

Tissue becomes ischemic when it is deprived of adequate blood flow. Ischemia causes pain in the area of the affected tissue and, in the case of muscle tissue, can interrupt muscular function. Left untreated, ischemic tissue can become infarcted and permanently non-functioning. Ischemia can be caused by a blockage in the vascular system that prohibits oxygenated blood from reaching the affected tissue area. However, ischemic tissue can be revived to function normally despite the deprivation of oxygenated blood because ischemic tissue can remain in a hibernating state, preserving its viability for some time. Restoring blood flow to the ischemic region serves to revive the ischemic tissue.

Although ischemia can occur in various regions of the body, often tissue of the heart, the myocardium, is affected by ischemia due to coronary artery disease, occlusion of the coronary arteries, which otherwise provide blood to the myocardium. Muscle tissue affected by ischemia can cause pain and lead to infarction of the tissue. Ischemia can be treated, if a tissue has remained viable despite the deprivation of oxygenated blood, by restoring blood flow to the affected tissue.

Treatment of myocardial ischemia has been addressed by several techniques designed to restore blood supply to the affected region. Coronary artery bypass grafting (CABG) involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2, August 1965, pp. 181–189. Although others have reported varying degrees of success with various methods of piercing the myocardium to restore blood flow to the muscle, many have faced common problems such as closure of the created channels. Various techniques of perforating the muscle tissue to avoid closure have been reported by researchers. These techniques include piercing with a solid sharp tip wire, hypodermic tube and physically stretching the channel after its formation. Reportedly, many of these methods still produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularization of the Heart by Laser", *Journal of Microsurgery*, Vol. 2, No. 4, June 1981, pp. 253–260. The laser was said to form channels in the tissue that were clean and made without tearing and trauma, suggesting that scarring does not occur and the channels are less likely to experience the closure that results from healing. U.S. Pat. No. 5,769,843 (Abela et al.) discloses creating laser-made TMR channels utilizing a catheter based system. Abela also discloses a magnetic navigation system to guide the catheter to the desired position within the heart. Aita U.S. Pat. Nos. 5,380,316, and 5,389,096 disclose another approach to a catheter based system for TMR.

Although there has been some published recognition of the desirability of performing transmyocardial revascularization (TMR) in a non-laser catheterization procedure, there does not appear to be evidence that such procedures have been put into practice. For example, U.S. Pat. No. 5,429,144 Wilk discloses inserting an expandable implant within a preformed channel created within the myocardium for the purposes of creating blood flow into the tissue from the left ventricle.

Performing TMR by placing stents in the myocardium is also disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open channel in the myocardium through which blood enters from the ventricle and perfuses into the myocardium.

Angiogenesis, the growth of new blood vessels in tissue, has been the subject of increased study in recent years. Such blood vessel growth provides new supplies of oxygenated blood to a region of tissue that has the potential to remedy a variety of tissue and muscular ailments, particularly ischemia. Primarily, the study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation*, 1998; 97:645–650. The authors noted that such treatment could be an approach to management of diffused coronary heart disease after alternative methods of administration have been developed.

Mechanical devices have been disclosed for delivering therapeutic substances to the myocardium. International patent publication no. WO 98/05307 by Local Med, Inc. discloses a method of using a conventional, rigid syringe and needle to access the myocardium and left ventricle to deliver a therapeutic substance such as an angiogenic factor.

SUMMARY OF THE INVENTION

The present invention provides a transthoracic drug delivery device that is specially configured to be precisely located in the myocardium for accurate placement of a therapeutic substance such as a drug. The device comprises a syringe having a delivery tube that is capable of penetrating the myocardium via the epicardium to access the left ventricle. Access to the heart is gained through the thorax. A pressure monitor associated with the device indicates the position of the distal tip of the delivery tube. It is noted that, throughout the discussion of the invention in the specification, "distal" is meant to indicate the direction along the access path of the device leading internal to the patient and "proximal" indicates the direction along the access path leading external to the patient. Pressure may be monitored through the delivery tube or through a separate pressure tube associated with the delivery tube. Specifically, the amount of pressure measured through the tube of the device informs the physician whether the distal port of the tube has penetrated the myocardium completely to reach the left ventricle. In the case of separate delivery and pressure tubes, the distance between the pressure tube opening and drug delivery tube opening is known, so the user can determine whether the drug delivery tube opening is still within the myocardium, and, therefore, appropriately placed to inject a drug into the myocardium. Multiple drug delivery tubes may be associated with the device to perfuse the drug more quickly through multiple ports into the myocardium. It is noted that throughout the specification "drug" includes all varieties of therapeutic substances that may be beneficial to the body, including pharmaceutical agents, genetically engineered substances or natural substances.

In another embodiment, a pressure sensing hypodermic tube, as in the first embodiment, is used to transthoracically access the heart and penetrate the left ventricle. However, the second embodiment is comprised of a single pressure sensing tube. The distal portion of the pressure tube is flexible and made controllable or steerable by mechanisms well known in the art of catheter manufacture such as a pull wire bonded to the distal end of the tube and extending proximally for manipulation outside the patient. After penetrating the left ventricle, the single pressure tube may be bent into a "J" configuration and the shaft withdrawn proximally to cause the curved tip of the J portion to penetrate the myocardium again, through the endocardial surface while moving in a proximal direction, similar to a fish hook. Entrance of the distal port of the pressure tube into the tissue results in a drop of measured pressure, indicating to the user that the distal tip of the pressure tube is within tissue, and, thus, appropriately placed to inject the drug or therapeutic substance being carried by the device.

After delivery of the therapeutic substance to a first location, the distal tip of the pressure tube may be backed out of the tissue by distal movement of the device into the ventricle and another location accessed. The steerable distal tip of the device permits the distal tip to be deflected through various angles relative to the longitudinal axis of the tube. Combining this range of movement with the rotational capability inherent in the device provides a locus of points about the penetration point into the ventricle where the distal tip of the needle can be placed into the myocardium to delivery therapeutic substances.

It is an object of the present invention to provide a drug delivery device that can access the myocardium and left ventricle of the heart transthoracically and accurately indicate the position of the distal tip of the device within the heart.

It is another object of the invention to provide a drug delivery device that is capable of delivering a therapeutic substance to the myocardium of the heart accurately and easily.

It is yet another object of the invention to provide a drug delivery device that is capable of delivering a therapeutic substance to the myocardium of the heart quickly via a plurality of delivery conduits.

It is yet another object of the invention to provide a drug delivery device that is capable of reaching a plurality of delivery locations in the myocardium with a single access to the heart.

It is yet another object of the invention to provide a drug delivery device for placement within the heart that is associated with a pressure sensor having adequate sensitivity to discern whether the pressure sensor port is within the myocardium or within the left ventricle.

It is yet another object of the invention to provide a delivery device that is configured to have a deflectable tip so that the reverse side of tissue having been accessed by the device can also be penetrated by the sharp tip of the device as the device is moved back along its access path.

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENT

Figure 1:
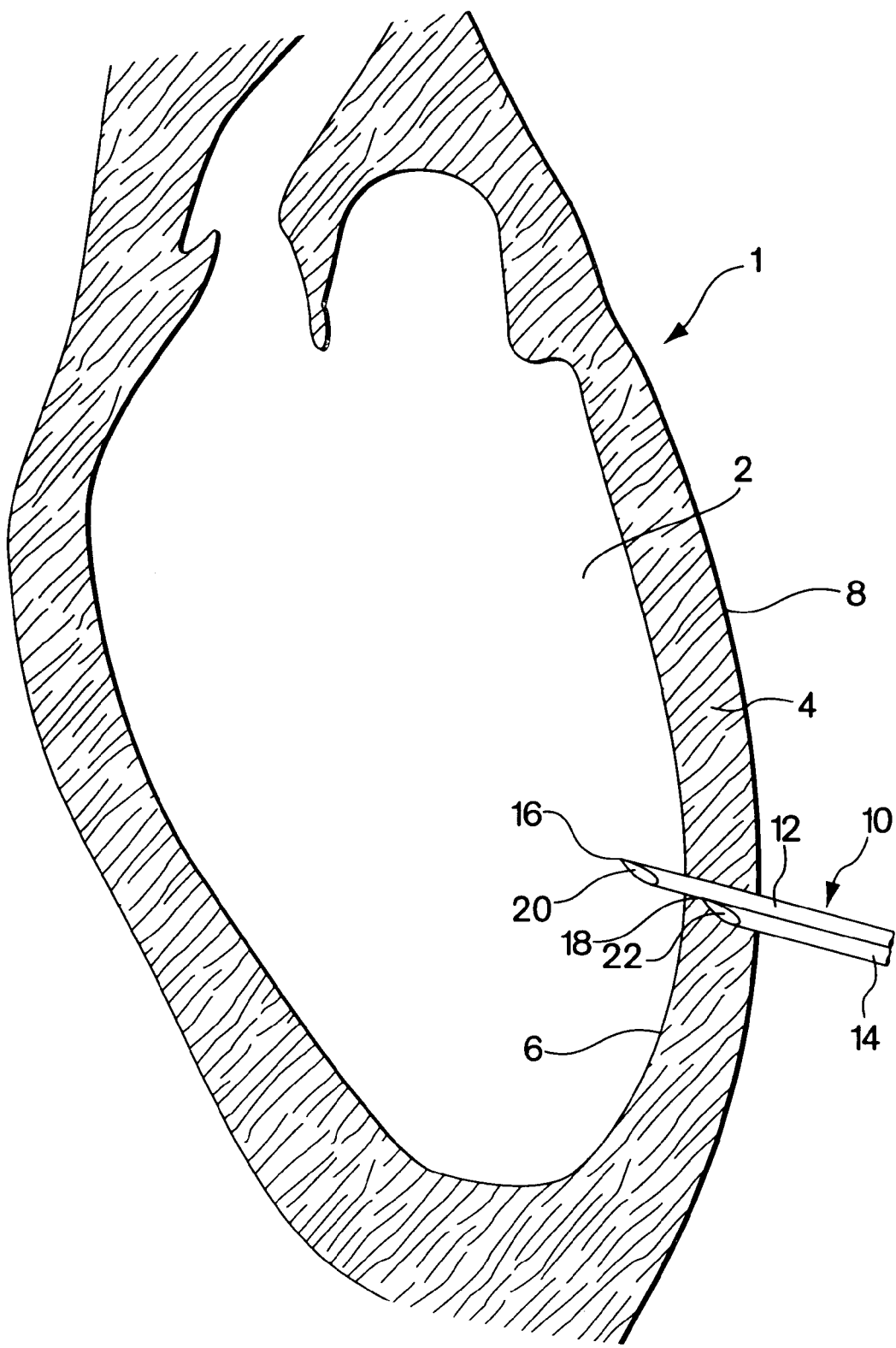
FIG. 1 is a diagrammatic, sectional illustration of the left ventricle of the human heart having the drug delivery device of the present invention inserted through the myocardial tissue.
Figure 2:
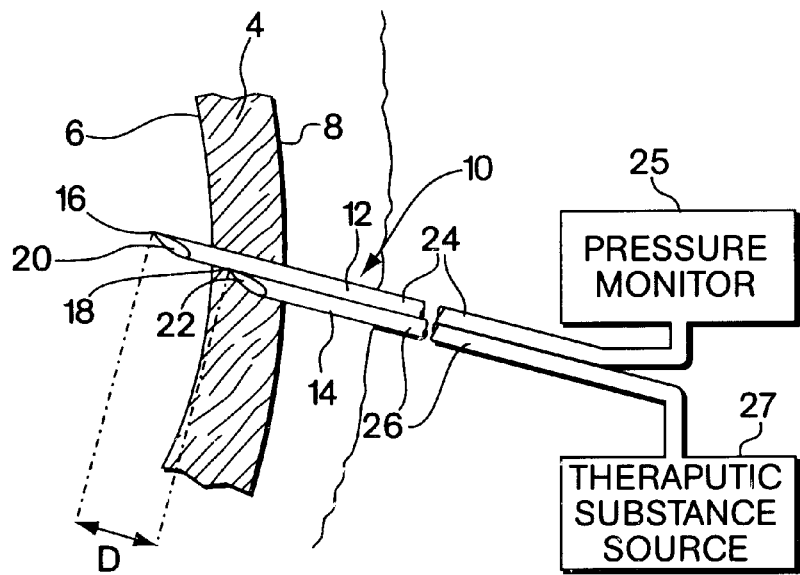
FIG. 2 is a detailed sectional illustration of a portion of myocardial tissue that has been penetrated by the drug delivery device of the present invention.

FIG. 1 shows a sectional view of the left ventricle of the heart 1 having been penetrated by the drug delivery device of the present invention. The multiple tube embodiment 10 is comprised of a pressure tube 12 for monitoring pressure and a delivery tube 14 for dispensing the therapeutic substance or drug into the myocardium 4. The tubes may comprise metal hypodermic tubing or any tubing capable of being configured to have sufficient strength and sharpness to penetrate tissue. The tubes are joined together side-by-side in parallel relationship, but are offset so that the pressure tube extends beyond the delivery tube. Both the pressure tube 12 and delivery tube 14 have sharpened distal tips 16 and 18 and open distal ports 20 and 22, respectively. The device is delivered through the thorax and epicardial surface 8 of the heart and advanced through the myocardium 4 until the pressure tube 12 penetrates the left ventricle 2. Alternatively, as will be described in further detail below, the tubes may be formed from relatively flexible material having rigid sharp inserts at the distal ends and the flexible tubes being temporarily fortified to resist buckling during delivery by an inner stiffening element that may be withdrawn after delivery.

The proximal end 26 of the delivery tube 14 is joined to a pressurized source of a therapeutic substance 27 such as may be provided by a syringe (not shown). The pressure tube is joined at its proximal end 24 to a pressure monitor 25 for measuring the pressure sensed at the pressure tube distal port 20. As the pressure tube is inserted through the tissue of the heart, measured pressure will be low; however, once the pressure port 20 reaches the left ventricle 2, measured pressure increases dramatically signaling the physician that the ventricle has been reached.

Figure 3:
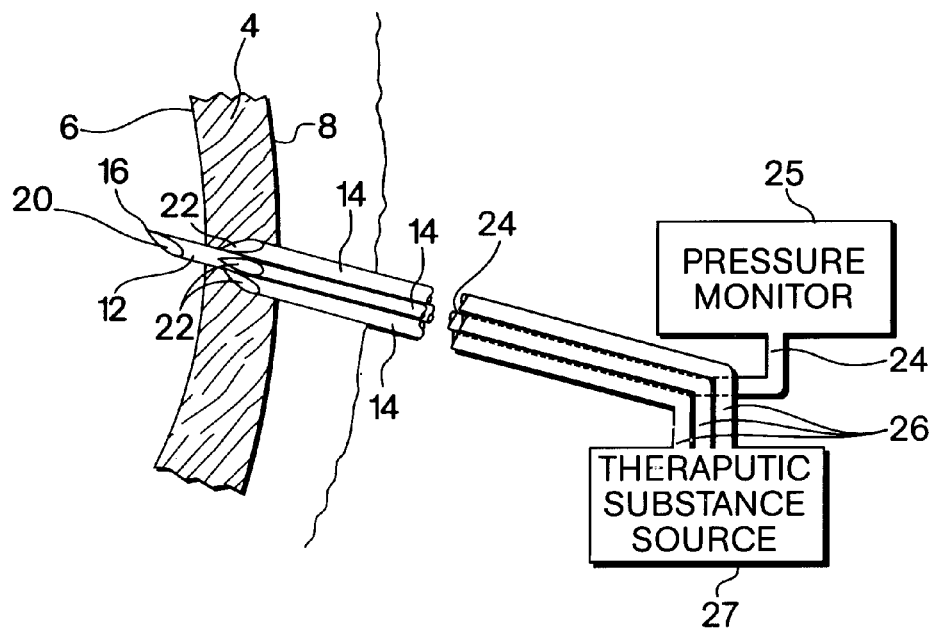
FIG. 3 is a detailed sectional illustration of a portion of myocardial tissue that has been penetrated by an alternate embodiment of the drug delivery device of the present invention.

The distance D between the relative longitudinal spacing of the pressure tube and delivery tube (measured from distal tip 16 to distal tip 18) is known. Therefore, at the moment during advancement of the device into the heart when pressure dramatically increases, not only is the position of distal tip 16 known (having penetrated the endocardial surface 6 to access the ventricle 2) but also, the position of the delivery tube distal tip 18 will be known relative to the endocardial surface 6. Therefore, if it is desired to deliver a therapeutic substance to a certain depth beneath the endocardial surface 6 of the myocardium 4, the pressure and delivery tubes 12 and 16 can be arranged relative to each other to provide that distance D between their distal tips 16 and 18. Upon penetration of the ventricle, the therapeutic substance can be discharged from the delivery port 22 at the desired distance beneath the endocardial surface 6. During this procedure, the pressure tube 12 may also be used to inject contrast media into the ventricle to help visualize the position of the device. FIG. 3 shows a variation of the multiple tube embodiment employing a plurality of delivery tubes, each spaced a distance beneath the distal tip of the pressure tube 12. The purpose of multiple delivery tubes is to provide increased drug delivery capability to surrounding myocardial tissue 4 with each penetration of the device into the heart.

Figure 4:
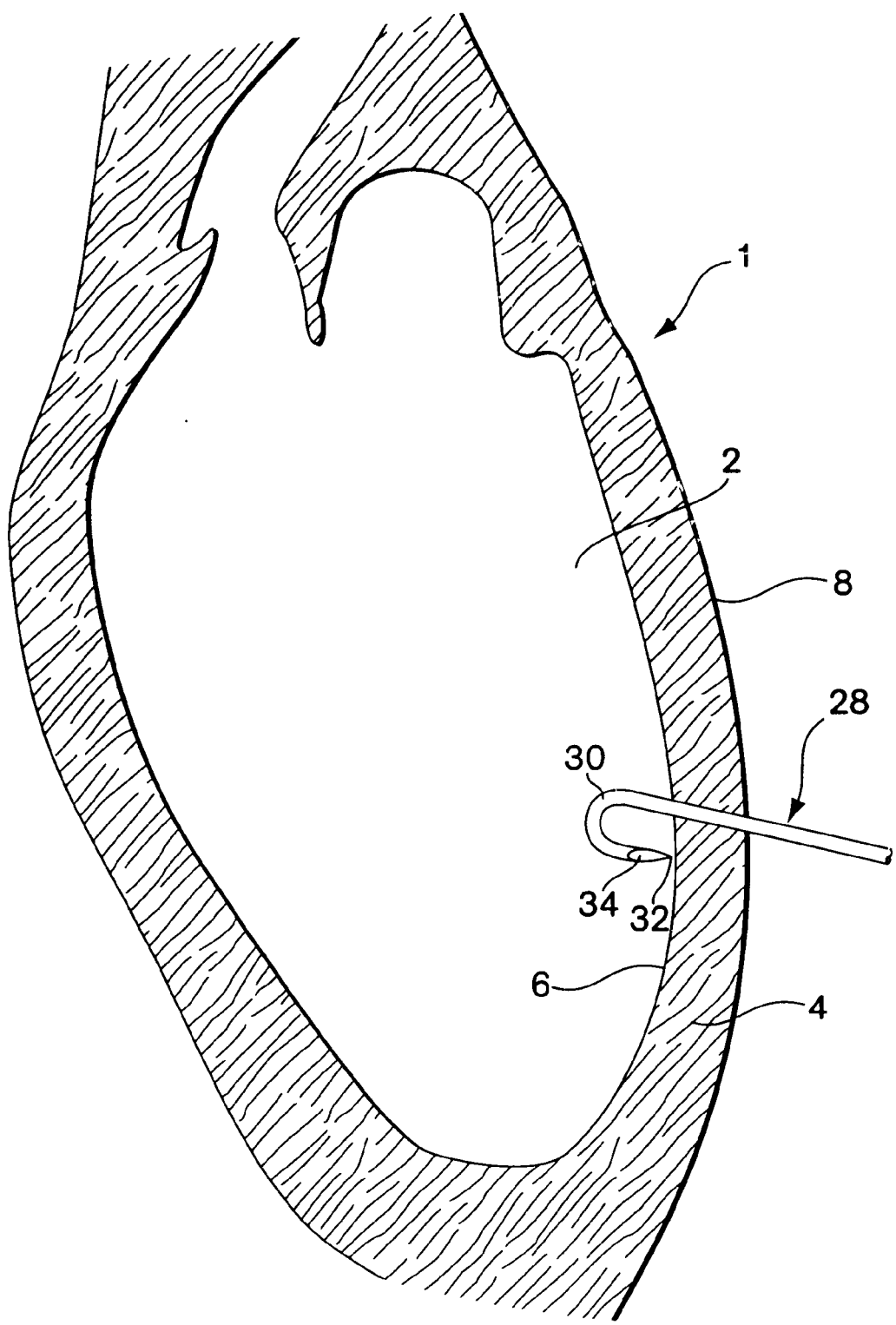
FIG. 4 is a diagrammatic, sectional illustration of the left ventricle of the human heart wherein the myocardium has been penetrated by a second embodiment of the drug delivery device.

The second embodiment of the drug delivery device further addresses the desirability of minimizing the number of times that the device must be inserted into the heart. A deflectable syringe tube 28 is shown in FIG. 4 protruding through the myocardium 4 into the left ventricle 2 of a human heart 1. After penetrating the myocardium, the distal portion 30 of the tube 28 may be deflected away from the longitudinal axis of the tube by as much as approximately 180°. The objective of providing such a large deflection is to permit the distal tip 32 of the tube to penetrate the endocardial surface 6 as the tube is withdrawn in a proximal direction from the ventricle 2. In the deflected configuration, the distal portion 30 of the tube is J-shaped and, therefore, pierces the tissue in similar fashion to a fishhook as it is withdrawn proximally. Once the distal port 34 has penetrated the myocardium, the therapeutic substance can be ejected through the port and into the tissue. The primary benefit provided by the deflectable tip tube is that multiple tissue locations can be reached with a single insertion penetration of the device into the heart.

Figure 5:
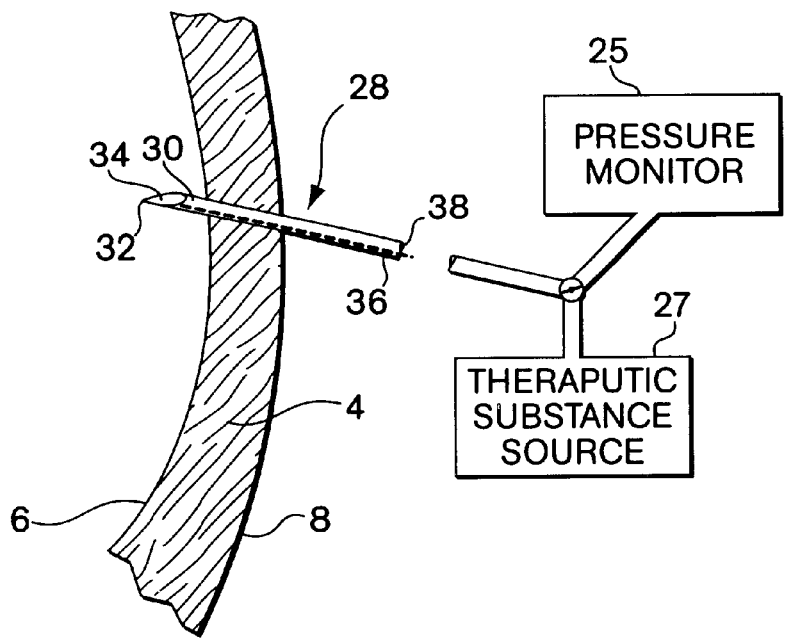
FIGS. 5–8 show a series of detailed sectional illustrations of a portion of the myocardium having been penetrated by the second embodiment of the delivery device.

As shown in FIG. 5, the tube should be inserted into the myocardium 4 while in a straight configuration. However, to be deflectable, at least the distal portion 30 of the tube must be flexible. Therefore, to provide sufficient longitudinal support during delivery through the heart tissue, a stiffening element 36 such as a stainless steel wire, may be advanced through the lumen 38 of the tube, extending to the distal tip 32. At least the distal portion 30 of the tube should be fabricated from a relatively flexible material, such as a relatively low density polymer, to provide adequate flexibility for bending when the tip is deflected. The distal tip 32 may comprise an insert of a more rigid material bonded to the flexible material, such as a high density polymer or stainless steel to provide a sharp, piercing profile.

Figure 6:
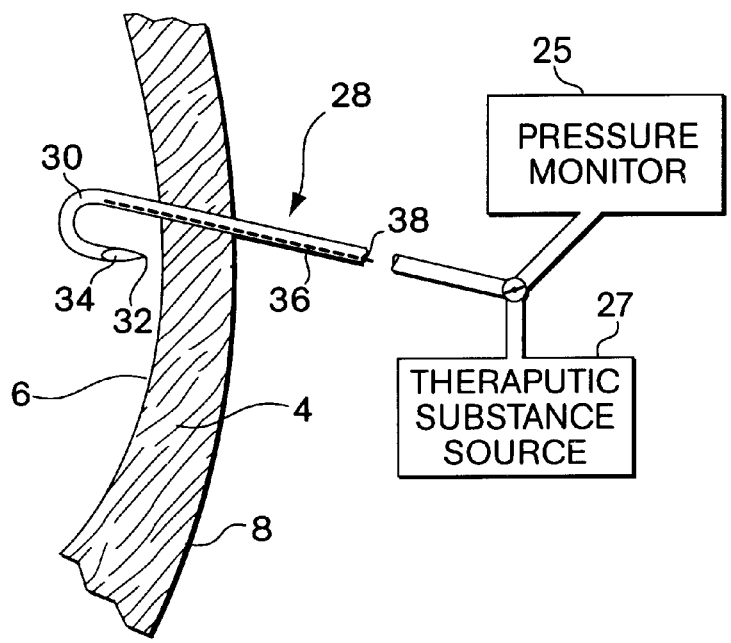

As shown in FIG. 6, after penetrating the myocardium 4, the stiffening element 36 is withdrawn proximally somewhat from the distal portion 30 of the tube 28 so that the tip 32 may be deflected to present its piercing distal tip 32 toward the endocardial surface 6 of the myocardium 4. The stiffening element 36 may, but need not be withdrawn completely from the tube to deflect the tip. The tip deflection may be actuated by a pull wire extending through the tube 28 and joined to the area of the distal tip 32. The pull wire extends proximally, out of the device so that it may be manipulated by the physician external to the patient. Pulling the pull wire puts tension on one side of the tube which tends to cause the flexible distal portion 30 to curve in the direction that the tension is being applied. Such pull wire arrangements are well known in the catheter art and are not discussed in detail here.

Figure 7:
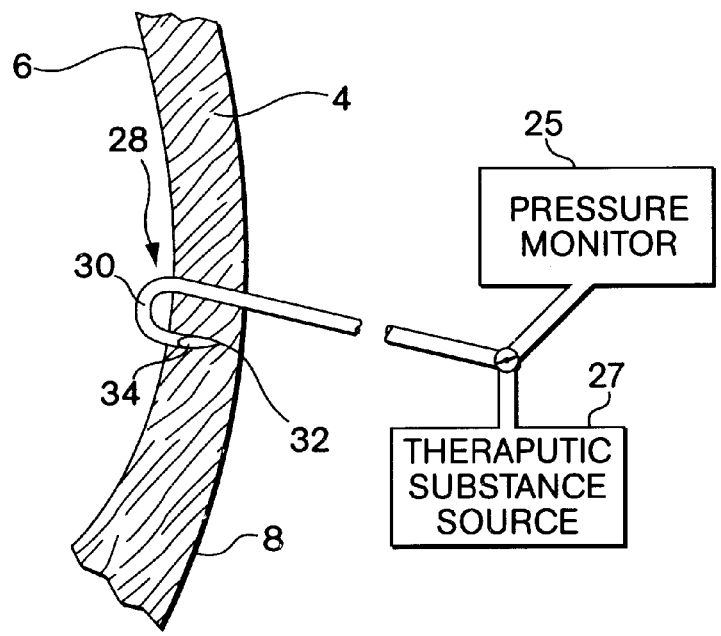

As shown in FIG. 7, the deflected tip is drawn proximally into the endocardial surface 6. In this configuration, the therapeutic substance is ejected from the port 34 into the tissue 4. After the desired quantity of therapeutic substance has been delivered to the location, the distal tip 32 is withdrawn from the myocardium 4 by moving the tube 28 distally slightly. The lumen of the tube 34 is in communication with a pressure monitor as was described in connection with the previous embodiment. Pressure sensing is useful in the present embodiment so that the physician can determine when the distal tip 32 of the tube has penetrated the myocardium 4 so that drugs can be delivered through port 34. In use, the pressure monitor indicates a high pressure when the port 32 is open to the ventricle. However, the pressure reading drops appreciably once the distal port 34 has become submerged within tissue indicating to the user that the distal tip is implanted.

Figure 8:
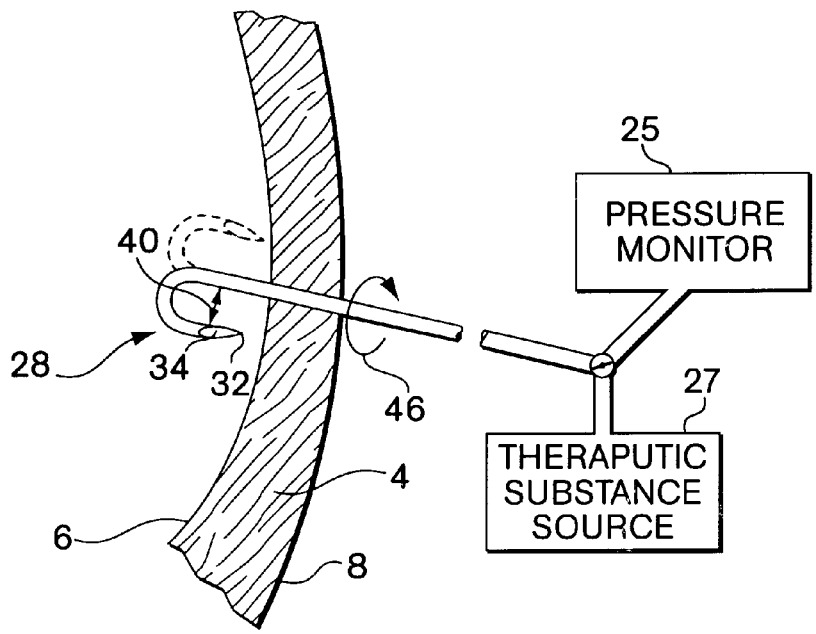

As shown in FIG. 8, the withdrawn distal tip 32 and distal portion 30 may be adjusted to locate a new tissue site in the myocardium to delivery the therapeutic substance. The amount of deflection of the distal tip, represented by arrow 40 may be adjusted to reach a new location within the myocardium 4 into which a therapeutic substance needs to be delivered. Additionally, the tube 28 may be rotated, as indicated by arrow 46 to provide a circle of points that are accessible by the deflectable tip tube. A possible new position for the distal portion 30 of the tube is shown in phantom in FIG. 8 to exhibit the steering capabilities of the device.

From the foregoing it will be appreciated that the invention provides a drug delivery device and method for delivering therapeutic substances to the myocardium quickly and accurately by accessing the thorax with a syringe and delivery tube device. Additionally, the present invention provides a device and method for accessing multiple points on the endocardial surface of the myocardium with a single penetration into the heart.

It should be understood, however, that the foregoing description of the invention is intended merely to be illustrative thereof and that other modifications, embodiments and equivalents may be apparent to those skilled in the art without departing from its spirit. Having thus described the invention, what we desire to claim and secure by Letters Patent is:

1. A method of delivering a therapeutic substance to a plurality of sites in the myocardium with a single penetration into the heart comprising:

introducing a tube having a deflectable distal portion and distal tip into the left ventricle of the heart;

deflecting the distal tip of the tube so that the tip faces the endocardium;

moving the tube in a proximal direction so that the distal tip penetrates the endocardium;

ejecting a therapeutic substance through the tube into the myocardium;

moving the distal tip from the myocardium by advancing the tube distally;

adjusting the position of the tip by changing the deflection angle of the tip or by rotating the tube to a new myocardial location;

moving the tube in a proximal direction to insert the distal tip into the myocardium at the new location;

ejecting a therapeutic substance from the tube into the myocardium.

2. A method of delivering a therapeutic substance to a plurality of locations within a myocardium as defined in claim 1 wherein the tube is equipped with a pressure sensor and the presence of the distal tip within myocardial tissue is determined by the change in pressure between the pressure indicated when the distal tip is in the myocardium versus the pressure indicated when the distal tip was in the ventricle.

3. A method of delivering a therapeutic substance to a plurality of locations within the myocardium as defined in claim 1 wherein the tube further comprises a stiffening element slidable within the tube and prior to introducing the tube, advancing the stiffening element at least through the deflectable distal portion of the tube to provide support while introducing the tube into the heart and then withdrawing the stiffening element proximal to the deflectable distal portion prior to deflecting the distal tip of the tube.

4. A method of delivering a therapeutic substance to a plurality of sites in the myocardium as defined in claim 1 wherein the tube is introduced through the epicardium of the heart to reach the left ventricle.

* * * * *